United States Patent
Roundhill et al.

[11] Patent Number: 6,139,501
[45] Date of Patent: Oct. 31, 2000

[54] COINCIDENT TISSUE AND MOTION ULTRASONIC DIAGNOSTIC IMAGING

[75] Inventors: David N. Roundhill, Woodinville, Wash.; Thanasis Loupas, Athens, Greece; Aline Laure Criton; David Rust, both of Seattle, Wash.

[73] Assignee: ATL Ultrasound, Inc., Bothell, Wash.

[21] Appl. No.: 09/327,693

[22] Filed: Jun. 8, 1999

[51] Int. Cl.[7] ............................................ A61B 8/00
[52] U.S. Cl. .................................................. 600/443
[58] Field of Search .................... 600/440–441, 600/443, 447, 453–456, 458; 128/916; 367/7, 11, 138; 73/625–626

[56] References Cited

U.S. PATENT DOCUMENTS

| | | |
|---|---|---|
| 4,182,173 | 1/1980 | Papadofrangakis et al. . |
| 4,274,422 | 6/1981 | Anderson et al. . |
| 4,559,952 | 12/1985 | Angelsen et al. . |
| 4,830,016 | 5/1989 | Tamoro et al. .......................... 600/455 |
| 4,848,354 | 7/1989 | Angelsen et al. . |
| 5,072,734 | 12/1991 | Takeuchi ................................ 600/455 |
| 5,349,524 | 9/1994 | Daft et al. ............................... 600/441 |
| 5,706,819 | 1/1998 | Hwang et al. ........................... 600/458 |
| 5,718,229 | 2/1998 | Pesque et al. ........................... 600/441 |
| 5,785,654 | 7/1998 | Iinuma et al. ........................... 600/441 |
| 5,785,655 | 7/1998 | Goodsell, Jr. et al. .................. 600/441 |
| 5,882,315 | 3/1999 | Ji et al. . |
| 5,951,478 | 9/1999 | Hwang et al. . |
| 5,961,460 | 10/1999 | Guracar et al. ......................... 600/441 |
| 5,961,462 | 10/1999 | Loupas et al. . |
| 6,036,643 | 3/2000 | Criton et al. ............................ 600/454 |
| 6,050,942 | 4/2000 | Rust et al. . |

*Primary Examiner*—Francis J. Jaworski
*Attorney, Agent, or Firm*—W. Brinton Yorks, Jr.

[57] ABSTRACT

Multi-mode ultrasonic images are formed by processing the ultrasonic echoes from a single transmit pulse in parallel to display both tissue and motion. In a preferred embodiment short transmit bursts are employed to produce echo ensembles for tissue motion imaging. At least one sequence of echoes of the ensemble is also B mode processed for display of tissue structure. Preferably both the B mode and motion processing are performed in parallel. A substantially constant pulse repetition frequency reduces artifact development when imaging in the two modes from the same transmit pulse.

21 Claims, 3 Drawing Sheets

COINCIDENT TISSUE AND MOTION ULTRASONIC DIAGNOSTIC IMAGING

This invention relates to ultrasonic diagnostic imaging systems and, in particular, to coincident tissue and motion ultrasonic diagnostic imaging using a common transmit signal.

The ultrasonic pulse echo imaging of tissue structures, whereby received echo signals are amplitude detected and arranged in an image in consideration of their time of flight, is commonly referred to as B mode imaging. B mode imaging can be done at relatively high frame rates of display, since only one transmit pulse is needed to form one or more image lines (scanlines) of the display. Following transmission of an ultrasonic beam in a given direction, a sequence of echoes is received from along the beam direction, from the near field to the far field. Echoes from a number of such beams are amplitude detected and displayed adjacent to each other in relation to their time of flight to form a two dimensional (2D) image of the structures which reflected the echoes.

The frame rate of display for B mode imaging is considerably faster than the frame rate of display for Doppler images such as power Doppler and colorflow images. This is because each Doppler image line must be interrogated a number of times in order to estimate the Doppler shift at points along the line. Each interrogation along the line acquires a full line of Doppler data, and the set of lines acquired over time is referred to as an ensemble. The ensembles of data are needed to estimate the Doppler shift by fast Fourier transform or autocorrelation at each point along the line. The number of transmit pulses required to gather a full ensemble of samples at each scanline reduces the frame rate of display below that required to acquire the same image frame for B mode display.

The time required to form an ultrasonic image is even greater when the image is formed of two imaging modes. Colorflow images, for example are formed by acquiring both a B mode image and a Doppler image, then presenting the final result as a composite of the two. In this way the flow of blood, displayed in the Doppler mode, is structurally depicted in its surrounding tissue and blood vessels by the B mode display. The time required to form such an image is the time required to transmit each B mode line and to receive echoes from along each line, plus the time required to transmit a Doppler line for each sample of the Doppler ensemble, and to receive echoes in response to each Doppler transmission. Different types of transmit pulses are used for B mode and Doppler to optimize the information of each mode of imaging. For B mode imaging short transmit pulses are preferred because of the high axial resolution of the resulting echo samples. For Doppler imaging, where sensitivity and narrow transmit bands are generally high priorities, relatively long transmit pulses are employed. The time to produce one frame of a multi-mode image is thus the total of the transmit and receive times of both the B mode and the Doppler signals, which is several multiples of the time required to scan the complete image field once.

When the transmit pulses for B mode and Doppler are time interleaved, the conventional technique to minimize beam steering changes, the time required to produce a single image frame is increased still further. This is because it is necessary to pre-condition the acoustic field for a particular type of pulse each time the type of pulse is changed to avoid image artifacts. For instance, suppose that a multi-mode image is to be produced using an eight-sample Doppler ensemble. Each line of the image must be scanned eleven times: a B mode conditioning pulse is followed by a B mode pulse, then a Doppler conditioning pulse is followed by the eight Doppler pulses. While the reduction in frame rate may be improved by using a small color box, thereby restricting Doppler scanning to only a portion of the full image width, the time required to form a complete image frame can become substantial when the color box occupies a substantial portion of the lateral dimension of the image. The frame rate of display is reduced correspondingly.

In accordance with the principles of the present invention, the total number of transmit-receive cycles required to form a composite B mode and motion image is reduced by sharing certain transmit-receive cycles for both B mode and motion imaging. The rf data received from a transmit pulse is used for both envelope-detection grayscale imaging and motion imaging. Compared to the conventional approach, better frame rates are attainable by coincident tissue and motion imaging from a common transmit pulse and the elimination of the need for conditioning pulses.

Figure 1:
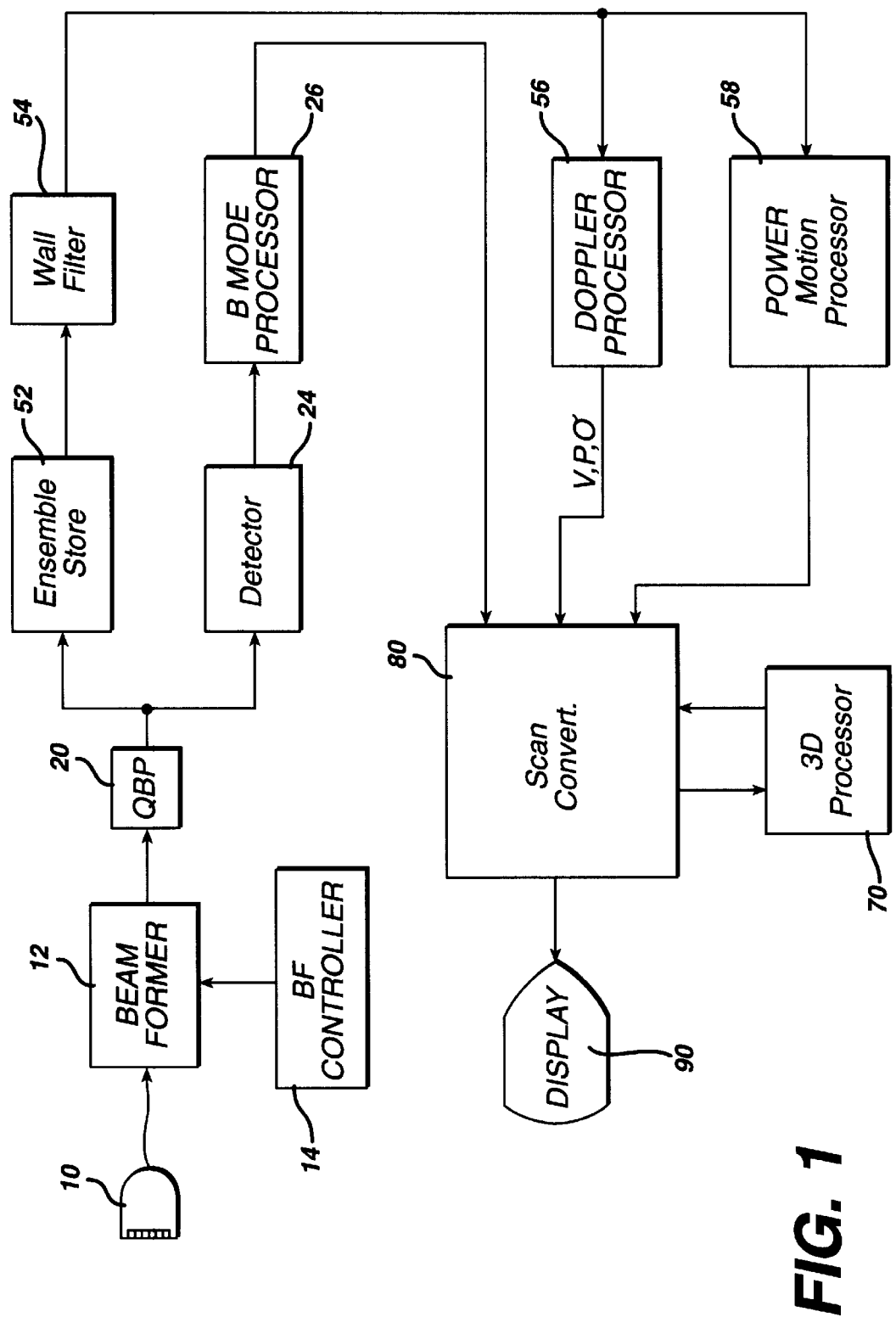
FIG. 1 illustrates in block diagram form an ultrasonic diagnostic imaging system constructed in accordance with the principles of the present invention.

Referring first to FIG. 1, an ultrasonic diagnostic imaging system constructed in accordance with the principles of the present invention is shown. An ultrasonic probe 10 includes an array transducer 18 which transmits beams of ultrasonic waves into the body and receives echoes reflected back to the transducer from cells and tissue in the body. The transmission by the probe is controlled by a beamformer 12 operated under control of a beamformer controller 14. The beamformer 12 controls the relative time at which each element of the array transducer is activated to transmit a controllably steered and focused ultrasound beam. The beamformer controller 14 is responsive to a user interface (not shown) to determine the frequency of the transmit waves and other characteristics of the transmitted waves such as amplitude and pulse length (number of transmitted cycles of the rf wave). Following each transmission by the transducer array 18 echoes are returned over time from increasing depths along the beam direction, referred to herein as a "line" of echo information. The line of echoes received by each element of the array transducer is delayed by the beamformer 14 to bring the received echoes across the array into phase coherence, which are then combined to form a sequence of coherent echo information along the line. In a preferred embodiment the beamformer is a digital beamformer which operates on digital samples of the received echoes to produce a sequence of echo samples along each image line.

The coherent echo samples are demodulated and filtered by a quadrature bandpass (QBP) filter 20 to produce I and Q quadrature components of each echo sample. In accordance with the principles of the present invention lines of echo samples are both B mode and Doppler processed. As an alternative to the use of a QBP filter, the echo samples may be quadrature demodulated, then filtered by two separate filters to impose different passbands for B mode and Doppler processing. Another alternative, and the one employed in the preferred embodiment discussed below, is to use different QBP filters for B mode and Doppler processing channels. The use of separate QBP filters permits each QBP filter to impose a number of different processing characteristics on echo signals destined for B mode or Doppler processing, including different bandwidths, center frequencies, filter lengths, and decimation rates. This embodiment allows one QBP filter to impose a narrow passband on echoes destined for Doppler processing, for instance, and the other QBP filter to apply a relatively broader passband on echoes destined for B mode processing.

For B mode processing the I,Q samples are amplitude detected by a detector 24 using the expression $(I^2+Q^2)^{1/2}$. The detected B mode signals are then B mode processed by a B mode processor 26 which performs functions such as compression and mapping of the B mode signals. The processed B mode signals are applied to a scan converter 80 for conversion to the desired display format and combining with motion display information. The composite multi-mode image is then displayed on a display 90.

The I,Q samples are also applied to an ensemble store 52 where multiple lines of echoes are stored to collect an ensemble of temporally discrete echo samples at each sample volume where motion is to be displayed. The completed ensembles are coupled to a wall filter 54 which eliminates unwanted echo components such as echo components from stationary tissue. The filtered ensembles are then coupled to either a Doppler processor 56 or a power motion processor 58. The Doppler processor 56 may employ different processing techniques such as fast Fourier transform (FFT) processing or correlation processing for the detection of motion of either flowing fluids (e.g., blood) or moving tissue (e.g., heart valves). In a preferred embodiment of the present invention autocorrelation processing is used. An ensemble of samples from each point on a Doppler image line can typically range up to 18 samples per ensemble. An ensemble of fewer samples may be used for display of moving tissue due to the high signal to noise ratio of tissue echoes and the fact that the wall filter is often bypassed when imaging the motion of tissue. The sample data is stored in quadrature I,Q form. An autocorrelator then multiplies adjacent samples in the sequence of samples in complex conjugate form and sums the products to produce a result in the form of I'+jQ'. Mathematically the autocorrelation process can be expressed as $$X' = \sum_{k=1}^{n-1} X_{k+1} \cdot X_k^* \quad (1)$$

where $X_k = I_k + jQ_k$ and n is the number of samples in the sequence. From the complex result the Doppler phase shift $\phi_D$ is calculated as the arc tangent of the quotient of Q' and I', or $$\phi_D = \tan^{-1} \frac{Q'}{I'} \quad (2)$$

The Doppler frequency shift $f_D$ is determined by multiplying the phase shift $\phi_D$ by the PRF and dividing by $2\pi$:

$$f_D = \phi_D \frac{PRF}{2\pi} \quad (3)$$

where PRF is the pulse repetition frequency of the transmitted Doppler pulses. The velocity of the motion is then estimated from the Doppler velocity equation $$v = \frac{f_D c}{2 f_o \cos\theta} \quad (4)$$

by assuming $f_o$ to be the center frequency of the transmitted waveform.

The Doppler processor 56 may also compute the Doppler power p, the Doppler signal intensity at each sample volume, and/or the variance a at each sample volume as is known in the art. The processed Doppler signals v, p or σ are generally mapped to a range of display color values and coupled to the scan converter where they are scan converted and overlay the structural B mode image in a multi-mode display.

The wall filtered signals may also be applied to a power motion processor 58 for processing and display of motion. The power motion processor generally operates on ensembles of fewer samples than the Doppler processor 56, and detects motion by differentiating temporally different samples from the same sample volume. The power motion processor 58 may also operate on ensembles which have bypassed the wall filter, since the effect of the processor 58 is to cancel echoes from stationary tissue, as stationary tissue is devoid of motion. The power motion processor 58 is described in detail in U.S. Pat. No. 5,718,229. The processed power motion signals are also generally mapped to a range of color display values, then coupled to the scan converter 80 for scan conversion and combining with a B mode structural image for multi-mode display.

The multi-mode images may also be processed for three dimensional display by a 3D processor 70, which forms three dimensional displays of multi-mode image data as described in U.S. Pat. Nos. 5,669,385; 5,720,291; and 5,860,924.

Figure 2:
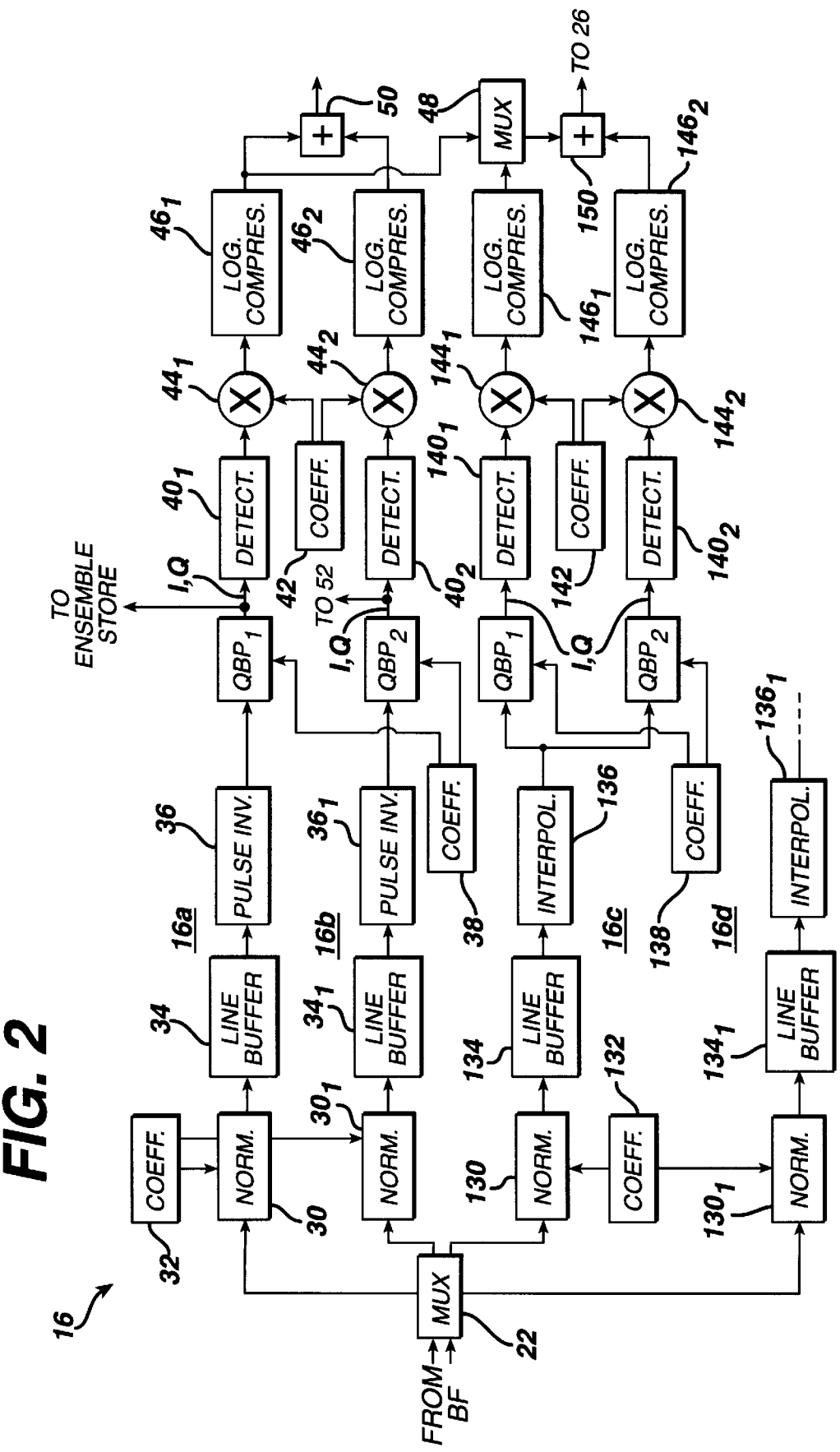
FIG. 2 illustrates a portion of the ultrasonic diagnostic imaging system of claim 1 which performs parallel processing of both B mode and motion signals from-a common transmit pulse.

The coherent echo information produced by the beamformer 12 may be processed in parallel for both B mode and motion display by the scanline processor 16 shown in FIG. 2. Image line echo data from the beamformer 12 is applied to a multiplexer 22. When the beamformer produces only a single scanline at a time, or scanline data in a time interleaved format, only a single digital data path is needed between the beamformer and the multiplexer 22. In the illustrated embodiment, two digital data paths are shown, enabling two simultaneously generated scanlines to be received by the multiplexer and coupled to the scanline processor 16 in parallel. Parallel processing of multiple scanlines is employed when the beamformer is performing multiline reception by producing two parallel coherent image lines in response to a single transmit pulse, as indicated by the two arrows from the beamformer. The two multilines may both be B mode processed, Doppler processed, power motion processed, or combinations thereof or the multilines may be processed differently by different channels of the scanline processor 16.

In the illustrated embodiment of FIG. 2, the scanline processor has four parallel processing channels, two of which (16a,16b) are configured for motion processing and two of which (16c,16d) are configured for B mode processing. Only the initial portion of channel 16d is shown and the balance of the channel is identical in construction to that of channel 16c. The operation of the scanline processor 16 when receiving a scanline which is to be both B mode and motion processed is as follows. The multiplexer 22 applies the scanline echo data in parallel to two channels 16a,16c of the scanline processor illustrated in FIG. 2. Each channel of the scanline processor has a normalization stage 30,30₁,130, 130₁ which multiplies the scanline data by a scale factor on a sample by sample basis to produce gain or attenuation that can vary with depth. The scale factor for each channel is provided by normalization coefficients stored in or generated by coefficient circuits 32,132, which in a preferred embodiment are digital memories. As the multiplying coefficients are changed as the sequence of scanline echoes progresses, depth dependent gain or attenuation is produced. The gain factors of the normalization stages also provide several other functions. One is to compensate for a transducer aperture which expands with depth of scan. As signals from an increasing number of transducer are used with increasing depth, the magnitude of the summed beamformed signals will increase. This increase is offset by reduced gain (increased attenuation) in the normalization stage, in proportion to the rate at which channels are added to the beamforming process, so that the resultant echo sequence will be unaffected by the changing aperture. The second function of the normalization stages is to equalize the nominal signal amplitudes of the channels when B mode processing is performed by several channels and frequency compounding is employed. The rate of gain change may be controlled by the rate at which the coefficients are changed for the multiplier of each normalization stage $30,30_1,130,130_1$.

After processing by the normalization stages 30,130, the echo signals in each channel 16a,16c are coupled to line buffers 34,134. The line buffers perform several functions. One is the storage of the first half aperture of beamformed echo signals for synthetic aperture formation. A second is to store a preceding scanline when the interpolators $136,136_1$ are operating to interpolate scanline data from consecutively received or laterally separate scanlines or when pulse inversion processors $36,36_1$ are combining consecutive echo sequences from oppositely phased transmit pulses along a scanline to separate harmonic signals by pulse inversion, as described in U.S. Pat. Nos. 5,706,819 and 5,951,478. Each of the interpolators $136,136_1$ can interpolate additional scanline data between two received scanlines, and the pulse inversion processors $36,36_1$ can separate harmonic and fundamental frequency components for tissue harmonic, contrast harmonic, or fundamental frequency imaging.

The echo signals in each channel are next coupled to quadrature bandpass filters (QBPs) in each channel. The quadrature bandpass filters provide three functions: band limiting the RF scanline data, producing in-phase and quadrature pairs of scanline data, and decimating the digital sample rate. Each QBP comprises two separate filters, one producing in-phase samples (I) and the other producing quadrature samples (Q), with each filter being formed by a plurality of multiplier-accumulators (MACs) implementing an FIR filter. The filter characteristic is determined by the values of the multiplying coefficients used by the MACs. Different sets of coefficients for different filter functions are stored in coefficient memories 38,138, which are coupled to apply selected coefficients to the multipliers of the MACs.

The coefficients for the MACs which form the I filter implement a sine function, while the coefficients for the Q filter implement a cosine function. For frequency compounding, the coefficients of the active QBPs additionally implement a sync function multiplied by a sine wave at the center frequency of the desired passband. In the instant case, when channel 16a is processing the echo signals for motion display and channel 16c is processing the same echo signals for B mode display, $QBP_1$ in channel 16a is producing I and Q samples of the scanline data in a passband which is formed about the nominal rf frequency of the motion signal. These I,Q samples are then transmitted to the ensemble store 52 for subsequent motion processing by the Doppler processor 56 or the power motion processor 58. In channel 16c, which is performing B mode processing, $QBP_1$ is producing I and Q samples of the scanline data in a first, lower frequency passband, and $QBP_2$ is producing I and Q samples of the scanline data in a second, higher frequency passband. Thus, the spectrum of the original broadband echo signals is divided into a relatively high frequency band and a relatively low frequency band. To complete the frequency compounding process, the echo data in the passband produced by $QBP_1$ of channel 16c is detected by a detector $140_1$ and the detected signals are coupled to one input of a summer 150. The echo data in the complementary passband produced by $QBP_2$ of channel 16c is detected by a detector $140_2$ and these detected signals are coupled to a second input of the summer 150. Following each detector in the channel is a gain stage formed by multipliers $144_1$ and $144_2$ which receives weighting coefficients from coefficient memory 142. The gain stages provide further gain adjustment in the two signal paths for optimal system performance and can be used to equalize the two frequency compounded passbands. Following each gain stage is a log compression processor $146_1,146_2$ comprising a lookup table. The output of each lookup table is proportional to the log of the signal input value. These lookup table are programmable so as to provide the ability to vary the compression curves, and the brightness and dynamic range of the scanline signals. When the signals of the two passbands are combined by the summer 150, the uncorrelated speckle effects of the two compounded passbands will cancel, reducing the speckle artifacts in the B mode image created from the signals. The speckle reduced B mode signals are then coupled to the B mode processor 26 for subsequent processing, grayscale mapping as needed, and display.

It is thus seen that the scanline processor 16 of FIG. 2 can process a single scanline of echo signals in parallel for both B mode and motion display in a single multi-mode image. The processor affords the capability of displaying both tissue and motion by their fundamental frequency content, both tissue and motion by harmonic frequency components, or one in fundamental and the other in harmonic frequencies. Further details of the scanline processor may be found in U.S. Pat. No. 6,050,942.

For multiline operation the echoes of one of the simultaneously produced scanlines are applied to channel 16a for motion processing and to channel 16c for B mode processing. The echoes of the other simultaneously produced scanline are applied to channel 16b for motion processing and to channel 16d for B mode processing.

Yet a further alternative is to process scanlines by channels 16a and 16b and by Doppler processor 56 for flow processing and display, and by power motion processor 58 for the concurrent display of tissue motion.

As explained above, the conventional approach to multi-mode imaging is to use a short, broad bandwidth transmit pulse for B mode imaging and a long, narrowband transmit pulse for Doppler imaging so as to optimize the reproduction of each kind of image information. However, the present inventors have found that the need for long pulses for Doppler imaging is of less concern when tissue motion is being imaged. This is due to the fact that the need for high sensitivity is reduced because of the relatively strong echoes returned from moving tissue as compared with the echoes from flowing blood cells. An additional benefit of tissue motion imaging is that only relatively short ensembles (few samples) are required to detect the Doppler signal or power motion signal from moving tissue. Since the Doppler imaging of tissue motion utilizes the relatively high amplitude and low frequency Doppler signals (as compared with flow echoes) of moving tissue, the normal wall filter characteristic, which passes low amplitude, high frequency Doppler returns to the exclusion of strong, stationary and slowly moving Doppler signals, is reversed. In one embodiment the wall filter is completely bypassed when imaging the motion of tissue with Doppler or power motion processing. In another embodiment the wall filter is set to block stationary (DC) motion effects when used with the power motion processor 58 so that the power motion processor will only need to operate over the dynamic range of moving tissue signals.

For similar reasons multi-mode images of power motion imaging and B mode imaging have also been found to perform well in coincident imaging.

The conventional multi-mode ultrasound system will use transmit pulses of only a few cycles for B mode imaging, and longer pulses of 4, 5 or more cycles for Doppler imaging. The present inventors prefer to use shorter pulses for coincident tissue Doppler imaging in accordance with the present invention. The present inventors use transmit pulses of 2–3 cycles for concurrent B mode and tissue Doppler imaging, which has been found to afford excellent axial resolution for both modes of imaging. For display, separate structural (B mode) and motion (Doppler, power motion) images can be composed and overlaid on the display screen, or pixels of a single image can be formed as a function of both structural and motion characteristics by modulating pixel characteristics such as brightness, color and hue as a function of structure and motion.

Since the echoes from moving tissue are of significant strength, the present inventors have found that short ensembles provide excellent results. High quality multi-mode tissue Doppler images have been produced using Doppler ensembles of three or four samples, and power motion imaging produces excellent results with only two samples in an ensemble. This compares with typical Doppler flow ensembles of up to sixteen samples in length. The short ensemble length is another reason for bypassing the wall filter when performing tissue Doppler imaging, as the number of taps of the filter would be relatively few in correspondence with the number of samples, thereby affording only a broad filter characteristic. Filtering tissue Doppler ensembles of limited length has been found to result in overestimation of tissue motion velocity, and a preferred technique for eliminating unwanted flow components is to perform thresholding above the level of flow signals and below the level of tissue signals in the Doppler processor 56.

A typical coincident scanning procedure is as follows. For each image line of interest, N pulses are transmitted and N lines of echoes are received, where N is the desired ensemble length. The ensemble length may be as short as N=2 for power motion imaging and N=2 to 4 for tissue Doppler imaging. The transmit pulses may be interleaved over a number of image lines (4–6 lines for power motion imaging and 2–4 lines for tissue Doppler imaging) and intraleaved to optimize the PRF by oversampling as described in [application Ser. No. 09/080,881]. The first line of echoes from each scanline is directed to both the motion processing signal path and the B mode signal path, where the echoes are preferably processed concurrently in parallel. To do so, the motion processing path should be set up in advance for motion processing, and the B mode path should be set up in advance for B mode processing. Thus, it is preferred that control of these two paths be independent.

To fully obviate the need for the pre-conditioning pulses, the present inventors have found it desirable to hold the PRF constant when doing motion and concurrent B mode and motion imaging. By holding the PRF interval including deadtime constant while doing concurrent imaging, there are no transient effects or differences between pulses and pulse intervals which would introduce artifacts into the image.

While it is only necessary to process one line of echoes along each image line for the B mode signal, it is also possible to process all echoes in the ensemble in the B mode path. In a parallel processing scheme, where the B mode path would otherwise be idle, this processing time can effectively be used to reduce noise by temporal averaging or filtering, or by other linear or nonlinear processing techniques. The results of this processing can also be applied to the motion processor to enhance its capabilities as, for instance, by providing a separate indication of motion detection at particular sample volumes.

The use of short ensemble lengths in concert with coincident imaging affords significant increases in frame rate of display. For example, suppose that three sample ensembles are used for coincident tissue Doppler and B mode imaging. In the conventional approach this would require 6N PRIs (pulse repetition intervals) for each image line: $T_{B\,mode}$=1N PRI plus $T_{TDI}$=3N PRI plus $T_{pre-cond.}$=2N PRI. But with coincident imaging only T=3N PRI are necessary, the length of the Doppler ensemble. Thus, the frame rate is doubled over the convention multi-mode approach.

Figure 3B:
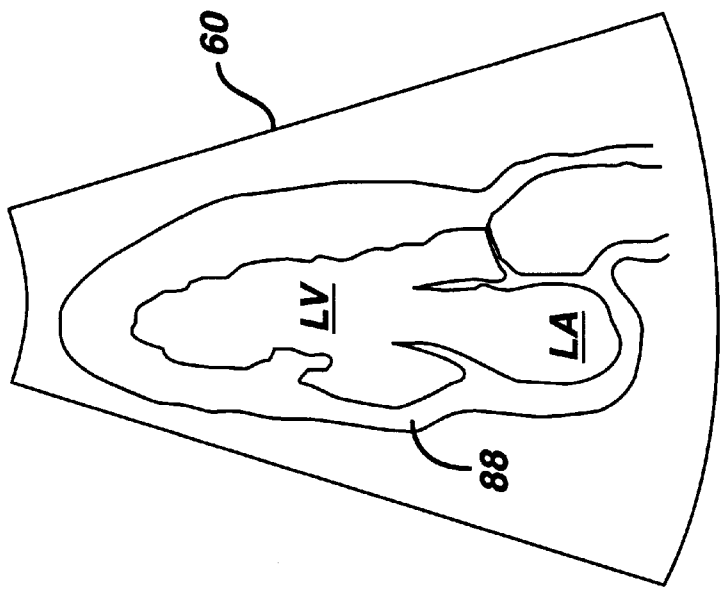
FIGS. 3a and 3b illustrate a colorflow image of vasculature with a color box and a tissue Doppler image of the heart.
Figure 3A:
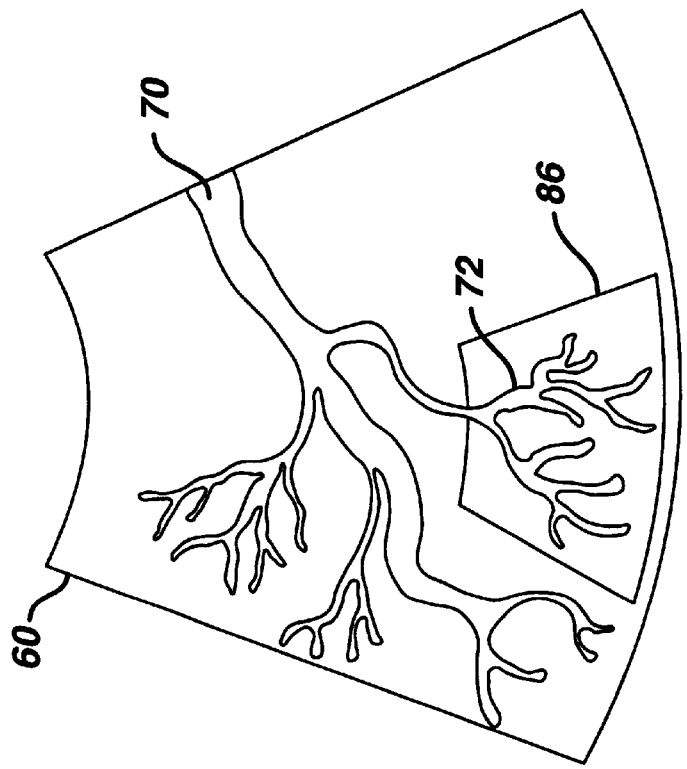

FIG. 3a illustrates an image frame 60 containing blood vessels 70. In this example only the blood vessels 72 in a color box 86 are Doppler imaged. Thus, it is only necessary to transmit and receive Doppler ensembles across the lateral dimension of the image occupied by the color box. The remainder of the image is scanned only by B mode pulses. Additional time savings can be had if the color box is near the skinline, requiring only shallow Doppler scanning of the color box.

By comparison, a typical tissue Doppler image is shown in FIG. 3b. This drawing illustrates a tissue Doppler image of the beating heart 88. Since the heart 88 occupies virtually the full image frame 60, a color box is often not employed since the color box would necessarily occupy the full frame 60. It is for this reason that substantial increases in frame rate are afforded when performing tissue Doppler imaging in accordance with the present invention.

What is claimed is:

1. A method for producing a multi-mode ultrasonic image comprising the steps of:

transmitting an ultrasonic wave which insonifies a given beam direction and receiving in response a scanline of echoes from said beam direction;

beamforming said received echoes to form coherent echo components; and processing said coherent components in a first, non-Doppler mode for display in an ultrasonic image; and processing said coherent components in a second, flow or motion mode for display in said ultrasonic image.

2. The method of claim 1, wherein said first mode is a B mode process and wherein said second mode is a motion detection process.

3. The method of claim 2, wherein said second mode is a Doppler process.

4. The method of claim 3, wherein said echoes are received from tissue in the body.

5. The method of claim 2, wherein said second mode is a power motion imaging process.

6. A method for producing a multi-mode ultrasonic image of both structure and motion comprising the steps of:

transmitting an ultrasonic wave from an array transducer and receiving in response a plurality of echo samples by elements of said array;

beamforming said received echo samples to form a coherent echo signal;

utilizing said coherent echo signal to display structure in an ultrasonic image; and utilizing said coherent echo signal to display motion in said ultrasonic image.

7. The method of claim 6, wherein said echo samples are received from tissue, and wherein said coherent echo signal is utilized to display motion of said tissue.

8. The method of claim 6, wherein said transmitted ultrasonic wave comprises less than five cycles at an rf transmit frequency.

9. The method of claim 8, wherein said transmitted ultrasonic wave comprises 2–3 cycles at an rf transmit frequency.

10. The method of claim 6, wherein said step of transmitting comprises transmitting a plurality of waves at a substantially constant pulse repetition frequency.

11. The method of claim 6, wherein said second step of utilizing comprises utilizing said coherent echo signal to detect Doppler power intensity.

12. A method for producing a multi-mode ultrasonic image of both structure and motion comprising the steps of:

transmitting a plurality of ultrasonic pulses from an array transducer along a given scanline;

receiving a sequence of echoes from along said scanline in response to each transmitted pulse;

motion processing a plurality of said sequences for the display of motion in said ultrasonic image; and B mode processing at least one of said sequences which is motion processed for the display of tissue in said ultrasonic image.

13. The method of claim 12, wherein the number of said sequences which are motion processed is at least two.

14. The method of claim 12, wherein the number of said sequences which are motion processed is four or less.

15. The method of claim 12, wherein the pulse repetition frequency of said plurality of transmitting and receiving steps is substantially constant.

16. The method of claim 12, wherein said step of receiving comprises producing sequences of echoes from along two laterally separate scanlines in response to a single transmitted pulse.

17. The method of claim 16, further comprising the step of interpolating echo values intermediate said laterally separate scanlines.

18. The method of claim 12, wherein said step of transmitting further comprises transmitting a plurality of ultrasonic pulses along a plurality of laterally separate scanlines;

wherein said step of receiving comprises receiving a sequence of echoes from along said scanlines; and further comprising the step of interpolating echo values intermediate laterally separate scanlines.

19. The method of claim 12, wherein said step of transmitting comprises transmitting a plurality of ultrasonic pulses at a fundamental transmit frequency; and wherein said step of receiving comprises receiving a sequence of echoes at a harmonic frequency of said fundamental frequency.

20. The method of claim 19, wherein said step of transmitting further comprises transmitting a plurality of ultrasonic pulses of different respective phases; and further comprising the step of separating harmonic and fundamental frequency echo components by pulse inversion.

21. A method for producing a multi-mode ultrasonic image of both structure and motion comprising the steps of:

transmitting an ultrasonic wave from an array transducer and receiving in response a plurality of echo samples by elements of said array;

beamforming said received echo samples to form a coherent echo signal; and parallel processing said coherent echo signal through a motion detection path and a tissue imaging path to produce both tissue and motion signals; and utilizing said tissue and motion signals to display a multi-mode image.

* * * * *